(12) United States Patent
Simpson et al.

(10) Patent No.: US 7,112,552 B2
(45) Date of Patent: Sep. 26, 2006

(54) COMPOSITIONS FOR SEPARATING MOLECULES

(75) Inventors: Daniel J. Simpson, Middleton, WI (US); Tonny Johnson, Madison, WI (US); Roderick G. Flemming, McFarland, WI (US)

(73) Assignee: Promega Corporation, Madison, WI (US)

( * ) Notice: Subject to any disclaimer, the term of this patent is extended or adjusted under 35 U.S.C. 154(b) by 98 days.

(21) Appl. No.: 10/689,176

(22) Filed: Oct. 20, 2003

(65) Prior Publication Data

US 2004/0127357 A1 Jul. 1, 2004

Related U.S. Application Data

(60) Provisional application No. 60/419,614, filed on Oct. 18, 2002.

(51) Int. Cl.
*B01J 20/22* (2006.01)
*B01J 20/10* (2006.01)
*B01J 20/283* (2006.01)
*B01J 29/04* (2006.01)
*C12N 11/00* (2006.01)

(52) U.S. Cl. ...................... 502/401; 502/407; 502/408; 502/415; 502/62; 502/63; 502/85; 435/174; 435/176

(58) Field of Classification Search ................. 502/407
See application file for complete search history.

(56) References Cited

U.S. PATENT DOCUMENTS

| | | | |
|---|---|---|---|
| 3,621,018 A | 11/1971 | Hindersinn et al. |
| 4,080,171 A | 3/1978 | Sano et al. |
| 4,220,726 A | 9/1980 | Warshawsky |
| 4,238,328 A | 12/1980 | Bowes et al. |
| 4,500,494 A | 2/1985 | Scher |
| 5,047,513 A | 9/1991 | Döbeli et al. |
| 5,175,271 A | 12/1992 | Thomas et al. |
| 5,217,866 A | 6/1993 | Summerton et al. |
| 5,250,188 A | 10/1993 | Bruening et al. |
| 5,700,642 A | 12/1997 | Monforte et al. |
| 5,922,545 A | 7/1999 | Mattheakis et al. |
| 5,981,194 A | 11/1999 | Jefferies et al. |
| 6,106,724 A | 8/2000 | McCulloch et al. |
| 6,194,550 B1 | 2/2001 | Gold et al. |
| 6,207,446 B1 | 3/2001 | Szostak et al. |
| 6,242,581 B1 | 6/2001 | Nelson et al. |
| 6,296,937 B1 | 10/2001 | Pryor et al. |
| 6,379,970 B1 | 4/2002 | Liebler et al. |
| 6,428,807 B1 | 8/2002 | MacFarlan et al. |
| 6,441,009 B1 | 8/2002 | Fernandez-Pol |
| 2001/0021535 A1 | 9/2001 | Nelson et al. |
| 2001/0039014 A1 | 11/2001 | Bass et al. |
| 2001/0046680 A1 | 11/2001 | Yu |
| 2002/0037532 A1 | 3/2002 | Regnier et al. |
| 2002/0040275 A1 | 4/2002 | Cravatt et al. |
| 2002/0058269 A1 | 5/2002 | Nock et al. |
| 2002/0182651 A1 | 12/2002 | Patricelli |

FOREIGN PATENT DOCUMENTS

| | | |
|---|---|---|
| WO | WO 91/12079 | 8/1991 |
| WO | WO 00/11208 | 3/2000 |
| WO | WO 02/37100 A2 | 5/2002 |

OTHER PUBLICATIONS

Frenzel, et al. "Novel purification system for 6xHis-tagged proteins by magnetic affinity separation", *Journal of Chromatography B*, 793(2003) 325-329.
Altin, et al., *Biochim. Biophys. Acta*, Aug. 6;1513(2):131-48 (2001).
Barret, et al., *Anal Chem.*, 73: 5232 (2001).
Brandt, et al., *Bioconjug. Chem.*, Mar.-Apr.;3(2):118-25 (1992).
Coulet, et al. "Immobilization of enzymes on metal-chelate regenerable carriers" *Biotechnology and Bioengineering*, 23: 663-668 (1981).
Erdogan & Houslay, *Biochem. J.*, 321: 165-175 (1997).
Fornasiero, et al., *Invest. Radio.*, Apr.;22(4): 322-7 (1987).
Frelinger, et al., *Biotechniques*, Nov.;31 (5): 1194 (2001).
Fujihara, et al., *Genes Cells*, Mar.;7(3): 343-50 (2002).
Gavin, et al., *Nature*, 415(6868): 141-147 (2002).
Gerber, et al., *Anal. Chem.*, 73: 1651 (2001).
Giriat et al., *Genet. Eng.*, (NY), 23: 171-199 (2001).
Goubran-Botros, et al., *Biochim. Biophys. Acta*, May 24;1074(1): 69-73 (1991).
Goubran-Botros, et al., *J. Chromotogr.*, Apr. 24;597(1-2):357-64 (1992).
Hainfeld, et al., *J. Struct. Biol.*, Sep.;127(2):185-98 (1999).
Haupt, Karsten, et al., *Anal. Biochem.*, Feb. 15;234(2):149-54 (1996).
He, Mingyue, *Nucleic Acids Res.*, Aug. 1;29(15):E73-3 (2001).
Hermason, Greg T., Mallia, Krishna; Smith; Paul K., *Immobilized Affinity Legand Techniques* Academic Press (1992).
Hochuli, et al., *J. Chromatogr.*, 411, 177-184 (1987).

(Continued)

Primary Examiner—Joseph D. Anthony
(74) Attorney, Agent, or Firm—Michael Best & Friedrich LLP

(57) ABSTRACT

The present invention provides compositions for the separation of metals or biomolecules such as polypeptides, nucleic acids, or endotoxins using modified solid supports.

16 Claims, No Drawings

OTHER PUBLICATIONS

Ito, et al., *J. Biol. Chem.*, 274, 9029-9037 (1999).
Kapanidis, et al., *J. Am Chem Soc*, Dec. 5;123(48):12123-5 (2001).
Kurt-Othmer Encyclopedia of Chemical Technology, vol. 21, 4$^{th}$ ed., Mary Howe-Grant, ed., John Wiley & Sons, p. 1021 (1997).
Laboureau, et al. *J. Mol. Recognit*. Nov.-Dec.;10(6):262-8 (1997).
Lamla, Thorsten, *FEBS Lett*, Jul. 27;502(1-2):35-40 (2001).
Maniatis, et al. Ausubel, Molecular Cloning, Cold Spring Harbor Laboratory (1982).
Motekaitis, et al., "New multidentate ligands. XV. Chelating tendencies of diglycine-N,N-diacetic acid, triglycine-N,N-diacetic acid, and tetraglycine-N,N-diacetic acid", *Inorganic Chemistry*, 13(3) 550-9 (1974).
Murata, et al., *Anal. Sci.* Mar.; 17(3):387-90 (2001).
Nanak, et al., *J. Mol. Recognit.*, Jan.-Apr.;8(1-2):77-84 (1995).
Porath, et al., *Nature*, 258, 598-599 (1975).
Principles of Gene Manipulation, Old and Primrose, 2$^{nd}$ ed., (1981).
Proffitt, et al., *J, Nucl, Med.*, Jan.;24(1):45-51 (1983).
Robert & Smith, *Curr, Opin, Chem, Biol,*, 6(3): 375-383 (2002).
Thess, et al., *J. Biol Chem.*, electronically published (Jul. 11, 2002).
Vosters, et al., *Protein Expr. and Purif.*, 3, 18-26 (1992).
Xu, et al., *Proc. Natl. Acad. Sci. USA*, 96, 151-156 (1999).
Zhu, Heng, et al., *Science*, Sep. 14;293(5537):2101-5 (2001).

COMPOSITIONS FOR SEPARATING MOLECULES

CROSS-REFERENCE TO RELATED APPLICATIONS

This application claims priority to U.S. Provisional Application No. 60/419,614, filed Oct. 18, 2002.

STATEMENT REGARDING FEDERALLY SPONSORED RESEARCH OR DEVELOPMENT

Not applicable.

BACKGROUND OF THE INVENTION

The present invention broadly relates to compositions useful in separating metal ions or other target material including, but not limited to, polypeptides, nucleic acids, and endotoxins, from non-target material.

BRIEF SUMMARY OF THE INVENTION

In one aspect, the present invention provides a composition comprising:

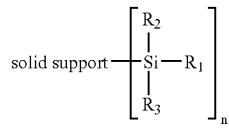

wherein $R_1$ is

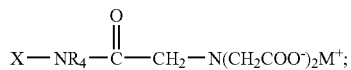

X is a substituted or unsubstituted alkylene moiety, a substituted or unsubstituted aralkylene moiety, or a substituted or unsubstituted arylene moiety;

$R_2$ and $R_3$ are independently selected from $R_1$, a hydrocarbon moiety, a substituted hydrocarbon moiety, a halogen atom, a hydrogen atom, a hydroxy, a thiol, an amine, a silanol bond to the solid support, a bond to another silane ligand, or O—Si—$Y_1Y_2Y_3$ wherein $Y_1$, $Y_2$ and $Y_3$ are independently selected from a hydrocarbon moiety or a substituted hydrocarbon moiety;

$R_4$ is selected from a hydrocarbon moiety, a substituted hydrocarbon moiety, and a hydrogen atom;

M is a metal ion; and n is an integer $\geq 1$.

All publications, patents and patent applications cited herein are hereby incorporated by reference in their entirety. In the case of conflict between the present disclosure and the incorporated publications, the present disclosure should control. It is understood that the numerical ranges given herein include all values from the lower value to the upper value and that disclosure of the range is a specific disclosure of all numbers and ranges therein.

These and other aspects of the present invention will be better appreciated by reference to the following drawings and detailed description.

DETAILED DESCRIPTION OF THE INVENTION

The compositions of the present invention comprise modified solid supports. Conveniently, the compositions of the present invention may be provided as kits that may be used to separate target material from non-target material.

The compositions of the present invention include nitrilotriacetic acid (NTA)-modified solid supports and metal-modified solid supports. Suitable solid supports for making the modified solid supports of the present invention include, without limitation, gels or hard support material, agarose, polyacrylamide, cellulose, plastics, polysaccharides, nylon, polystyrene, latex methacrylate, silica, aluminum oxide, electrodes, membranes and derivatives thereof.

Suitable silica solid supports include, but are not limited to, siliceous oxide, magnetic silica particles, solid silica such as glass or diatomaceous earth and the like, or a combinations of silica materials (see, e.g., preparation of silica discussion in Kurt-Othmer Encyclopedia of Chemical Technology, Vol. 21, 4th ed., Mary Howe-Grant, ed., John Wiley & Sons, pub., 1997, p. 1021.) As discussed in the examples below, suitable silica gels are available commercially from suppliers such as Silicycle (Quebec City, Canada), J. T. Baker (Phillipsberg, N.J.), and Sigma-Aldrich, (St. Louis, Mo.). Suitable silica gels for the compositions and methods of the invention are further described in the examples below. Other suitable silica supports include crystalline or vitreous silicas, such as quartz, vitreous silica, controlled pore glass particles, and glass fibers.

Silica gel may be characterized by pore diameter, particle size, or specific surface area. Suitable silica gels have a pore diameter from about 30 to about 1000 Angstroms, a particle size from about 2 to about 300 microns, and a specific surface area from about 50 $m^2/g$ to about 1000 $m^2/g$. Suitable silica gels include, for example, those having a pore diameter of about 40 Angstroms, about 60 Angstroms, and about 150 Angstroms; those having a particle size of about 2 to about 25 microns, about 5 to about 25 microns, about 15 microns, about 63 to about 200 microns and about 75 to about 200 microns; and those having a specific surface area of about 300 $m^2/g$, about 500 $m^2/g$, about 550 $m^2/g$, about 675 $m^2/g$, and about 750 $m^2/g$.

Conveniently, a solid support according to the present invention may comprise magnetic silica particles. Magnetic silica particles comprise a superparamagnetic core coated with a hydrous siliceous oxide adsorptive surface (i.e. a surface having silanol or Si—OH groups). Suitable, commercially available magnetic silica particles include MagneSil™ particles available from Promega Corporation (Madison, Wis.). The preparation of magnetic silica particles suitable for use as a support according to the present invention is described in U.S. Pat. No. 6,296,937.

Suitable cellulose supports include, but are not limited to, nitrocellulose and cellulose acetate.

Suitable membranes include, but are not limited to, glass fiber membranes impregnated with silica.

Suitable aluminum oxide solid supports include, but are not limited to, Brockmann aluminum oxides that are about 150 mesh and 58 angstroms.

The solid support, as described herein, suitably includes at least one free hydroxyl group so that when the solid support is contacted with an aminosilane compound, the silicon atom of the aminosilane compound is covalently bound to the solid support by at least one silanol bond to form an amine-modified solid support.

Aminosilane compounds are commercially available through suppliers such as United Chemical Technologies, Inc. (Bristol, Pa.). Suitable aminosilane compounds have the general formula

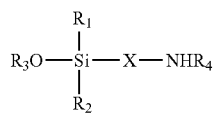

wherein X is an alkylene moiety of up to 20 carbon atoms that may be saturated, unsaturated, branched, linear, or cyclic, for example, methylene, ethylene propylene, nonylene, or an aralkylene moiety of up to 20 carbon atoms in which the alkyl portion may be saturated, unsaturated, branched, linear, or cyclic or an arylene moiety of up to 20 carbon atoms, and wherein X may be unsubstituted or substituted as defined below with respect to hydrocarbon moiety;

$R_1$ is a hydrocarbon moiety, or a substituted hydrocarbon moiety;

$R_2$ and $R_3$ are independently selected from $R_1$, a hydrocarbon moiety, a substituted hydrocarbon moiety, a halogen atom, a hydrogen atom, a hydroxy, a thiol, an amine, a silanol bond to the solid support, a bond to another silane ligand, or O—Si—$Y_1Y_2Y_3$, wherein $Y_1$, $Y_2$ and $Y_3$ are independently selected from a hydrocarbon moiety, or a substituted hydrocarbon moiety; and $R_4$ is a hydrocarbon moiety, a substituted hydrocarbon moiety, or a hydrogen atom.

The term "hydrocarbon moiety" as used herein refers to an alkyl group of up to 20 carbon atoms (i.e., alkanes, alkenes or alkynes) that may be saturated, unsaturated, branched, linear, or cyclic; or an aralkyl group of up to 20 carbon atoms in which the alkyl portion may be saturated, unsaturated, branched, linear or cyclic; or an aryl group of up to 20 carbon atoms. Suitably, the hydrocarbon moiety has from 2 to 15 carbon atoms, or from 5 to 10 carbon atoms. A "substituted hydrocarbon moiety" refers to a hydrocarbon moiety, as defined herein, in which at least one carbon atom is substituted with an oxygen, a sulfur, or a nitrogen atom. The substituent may be, for example, oxo, alkoxy, alkoxycarbonyl, hydroxy, esters, thioethers, amino, alkylamine, or carbamoyl.

Examples of suitable aminosilane compounds useful in the practice of the present invention include, but are not limited, to aminopropylsilane, propylethylenediaminesilane, N-[3-(trimethoxysilyl)propyl]ethylenediamine, and N-[3-(trimethoxysilyl)propyl]diethylenetriamine.

An NTA-modified solid support, as described herein, may be produced by contacting a solid support having a free —$NH_2$ moiety to form an amide bond between nitrilotriacetic acid and the amine group of the support. Nitrilotriacetic acid acts as a chelating agent capable of forming stable complexes with polyvalent metal ions.

Any solid support is acceptable provided that it has an amine moiety that can be modified or can be made to contain a modifiable amine group. Suitable solid supports for use in the manufacture of NTA-modified solid supports have a plurality of free $NH_2$ moieties. One skilled in the art would be able to attach a free amine functionality to a solid support by chemically modifying the surface of the solid support. See, e.g., Greg T. Hermason, A. Krishna Mallia, Paul K. Smith, *Immobilized Affinity Legand Techniques*, Academic Press (1992). In addition, suitable solid supports with free $NH_2$ moieties capable of binding to the NTA to form an NTA-modified solid support according to the present invention are commercially available. These include, but are not limited to, agarose-based supports sold by Sigma-Aldrich Inc. (St. Louis, Mo.); latex-based supports sold by International Dynamics Corporation, (Longwood, Fla.); polystyrene-based supports sold by Bangs Laboratories Inc., (Fishers, Ind.); Spherotech, (Libertyville, Ill.); and Dynal Biotech, (Lake Success, N.Y.).

In another aspect, the present invention provides metal-modified solid supports. The metal-modified solid support, as described herein, may be produced by contacting the NTA-modified solid support described above with a metal ion solution to form the metal-modified solid support. The metal ion solution may be comprised of metal ion salts, wherein the salts include, but are not limited to chloride, sulfate, phosphate, acetate, carbonate, citrate, acetylacetonate, bromide, fluoride, iodide, nitrate and oxalate salts. The metal concentration may be from less than about $10^{-6}$ M to about 1 M. Typically, the metal ion concentration in solution may be in the range of about 0.1 M to about 1 M. It is envisioned that the metal ion solution may be composed of only one metal ion or a mixture of different metals. Suitably, a tetradentate complex may be formed between the metal ion and the NTA-modified solid support. See, e.g., *New multidentate ligands. XV. Chelating tendencies of diglycine-N,N-diacetic acid, triglycine-N,N-diacetic acid, and tetraglycine-N,N-diacetic acid*, Inorganic Chemistry (1974), 13(3), 550–9.

By a "metal ion" it is meant any metal with a oxidation state between +1 and +6. Suitably, the metal may be nickel, copper, cobalt, iron, zinc, or gallium. Additionally the following metal ions are considered suitable for the present invention: iron (III), copper (II), cobalt (II), nickel (II), zinc (II), cerium (III), magnesium (II), calcium (II), galium (III), chromium (III), indium (III), lanthanum (III), lutetium (III), scandium (III), thallium (III), ytterbium (III), thorium (IV), uranate (II) silver (I), gold (I) and copper (I). One skilled in the art would be able to select a suitable metal depending on the material to be separated. Also, it is envisioned that the bound metal ions may be stripped from the metal-modified support with a chelating agent, such as ethylene diamine tetraacetic acid (EDTA), therefore allowing the regeneration of the NTA-modified solid supports.

As one of skill in the art will appreciate, the NTA-modified and metal-modified solid supports may be used in a variety of applications as described herein.

The NTA-modified solid support may be used to prepare chelating immuno-stimulating complexes using metal chelating approaches as described in U.S. Pat. No. 6,428, 807.

It is also envisioned that the NTA-modified solid support may be used to remove toxic metals from drinking water, the environment, or blood of individuals with diseases caused by metal exposure. For example, the NTA-modified solid may be used to remove and/or recover potentially harmful or toxic metals, such as aluminum, arsenic, bismuth, antimony, excess calcium, excess iron, gold, zinc, magnesium, mercury, cadmium, lead, copper and silver, from industrial waste waters and waters destined for human consumption.

The NTA-modified solid supports of the present invention may also be useful in a number of other applications in which it is desirable to extract, deactivate or remove metals from fluids, e.g., removing calcium from plasma to convert the plasma to serum, or wiping up spills of radioactive metallic ions in laboratories. The NTA-modified supports may be employed to remove toxic metals from individuals with lead or mercury poisoning.

Interference with or depletion of certain metal ions has been reported as having a role in health conditions. Accordingly, the NTA-modified solid supports of the present invention may be used as a diagnostic tool for detecting and extracting metal-associating molecules indicative of the disease state or predisposition to a disease.

It is envisioned that metal-modified solid supports may be used to separate target material (e.g., polypeptides or nucleic acids) from non-target material in a starting solution. The metal-modified solid support may be used alone, or in conjunction with other purification methods, including methods using an amine-modified solid support.

The metal-modified solid support may be utilized in separating his-tagged polypeptides from non-target material in a starting solution. The metal-modified solid support may also be used in removal of endotoxins from a starting solution. Suitably, the term endotoxin refers to the lipopolysaccharide complex associated with the outer membrane of Gram-negative bacteria such as *E. coli, Salmonella, Shigella, Pseudomonas, Neisseria, Haemophilus*, or any other endotoxin-producing pathogens.

The metal-modified solid support may also be used in the identification of low-abundance proteins, identification of membrane proteins and phosphorylated proteins. The metal-modified solid support may also be used in the identification and quantitation of polypeptide-polypeptide interactions where the general classes of suitable detectable moiety or label includes but is not limited to a dye, a fluorophore, a nanoparticle that may be generally attached anywhere on the target material or specifically attached to the end of the target material (i.e., N-termini, C-termini or both N-termini and C-termini of peptides) to be detected and quantified.

The metal-modified solid support may also be used in isolating polypeptide-polypeptide complexes; screening for polypeptide function; isolating antibodies, antigens and antibody-antigen complexes; quantitating affinity-tagged polypeptides; diagnostic screening for diseases; antibody screening; antagonist and agonist screening for drugs; reporter gene assays; producing polypeptide expression libraries, producing polypeptide libraries from cells; producing polypeptide microarrays; screening genetically engineered enzymes; or co-isolating interacting molecules (i.e., co-factors).

Metal-modified solid supports of the present invention will be useful in studies of polypeptide-polypeptide interactions. The metal-modified solid support may be used to reduce endotoxin concentrations in solution. The metal-modified solid support may be used to separate phosphorylated proteins from a starting solution.

The metal-modified solid support may be utilized in many applications, including, but not limited to, tissue profiling and cell profiling.

The following examples illustrate procedures for practicing the invention. Those skilled in the art of this invention will appreciate that the detailed description of the invention is meant to be exemplary only and should not be viewed as limiting the scope of the invention.

EXAMPLES

Example 1

Preparation Of Metal-Modified 3-[[[Bis(carboxymethyl)amino]acetyl]-amino]propyl Silica Magnetic Particles.

a) Preparation of 3-Aminopropyl-Modified Magnetic Silica Particles.

3-Aminopropyl-modified magnetic silica particles were prepared as follows. A 50-ml aliquot of 3-aminopropyltrimethoxysilane was added to a stirred solution of methanol (900 mL) followed by addition of water (50 mL). The mixture was added to 100 g of magnetic silica particles (MP-50, W. R. Grace, Columbia, Md.). The particles were kept in suspension for 4 hr at room temperature using intermittent agitation. The residual methanol/silane/water solution was removed and the support particles were washed with 3×1.2 L of water then resuspended in 1 L of methanol. The 3-aminopropyl-modified magnetic silica particles were collected by filtration and dried under vacuum. Elemental analysis confirmed the composition of the 3-aminopropyl-modified magnetic silica particles: C, 0.75; H, 0.64; N, 0.30.

b) Preparation of 3-[[[Bis(carboxymethyl)amino]acetyl]amino]-propyl Magnetic Silica Particles.

3-[[[Bis(carboxymethyl)amino]acetyl]amino]-propyl magnetic silica particles were made by first suspending 3-aminopropyl-modified magnetic silica particles (100 g), prepared as described above, in N,N-dimethylacetamide (600 mL), adding triethylamine (31 ml, 210 mmoles), and mixing thoroughly. 200 mmoles of 2,6-diketo-N-carboxymethyl-morpholine (prepared according to U.S. Pat. No. 3,621,018) in 400 ml of N,N-dimethylacetamide was added and the resulting mixture was kept in suspension for 4 hr at room temperature. The unreacted N,N-dimethylacetamide/anhydride/triethylamine solution was removed and the particles were washed with 3×1.2 L of water. Elemental analysis confirmed the composition of 3-[[[bis(carboxymethyl)amino]acetyl]amino]-propyl-modified magnetic silica particles: C, 1.06; H, 0.61; N, 0.17.

c) Preparation of Nickel (II) 3-[[[Bis(carboxymethyl)amino]-acetyl]amino]propyl Magnetic Silica Particles.

Nickel (II) 3-[[[bis(carboxymethyl)amino]-acetyl]amino]-propyl magnetic silica particles were prepared by suspending 100 grams of 3-[[[bis(carboxymethyl)amino]-acetyl]amino]-propyl magnetic silica particles, prepared as described above, in a 250 mM nickel (II) chloride solution (1 L) for 4 hours at room temperature. The excess nickel solution was removed and the resulting solid support was washed with five times with water.

Modified particles similar to those described above in Example 1(a)–(c) were prepared using starting particles other than magnetic silica particles from W. R. Grace. Other silica gels that have been used in steps (a)–(c) were supplied by: Sigma-Aldrich Corp (St. Louis, Mo.) (23,681-0, 23,682-9, and 23,684-5); Silicyle Inc. (Quebec, Calif.) (S10030M, 10040M, 100300T, S10040T, and R10030M); or J. T. Baker (Philipsburg, N.J.) (7314-02 and 7315-20). The commercial silica gels contained particles having diameters in the range of about 5 to about 500 microns, and pore sizes in the range of about 40 to about 1000 Angstroms.

d) Preparation of Colbalt (II) 3-[[[Bis(carboxymethyl)amino]-acetyl]amino] propyl Magnetic Silica Particles.

Cobalt (II) 3-[[[bis(carboxymethyl)amino]-acetyl]amino]-propyl magnetic silica particles were prepared by suspending 100 mg of a 3-[[[bis(carboxymethyl)amino]-acetyl]amino]-propyl magnetic silica particles, prepared as described above, in a 250 mM cobalt (II) chloride solution for two minutes at room temperature. The excess cobalt solution was removed and the resulting magnetic silica particles were washed 5 times with water.

e) Preparation of Copper (II) 3-[[[Bis(carboxymethyl)amino]-acetyl]amino] propyl Magnetic Silica Particles.

Copper (II) 3-[[[bis(carboxymethyl)amino]-acetyl]amino]-propyl magnetic silica particles were prepared by suspending 100 mg of a 3-[[[bis(carboxymethyl)amino]-acetyl]amino]-propyl magnetic silica particles, prepared as described above, in a $CuCl_2$ (250 mM) solution for two minutes at room temperature. The copper solution was removed and the resulting magnetic silica particles were washed three times with water.

f) Preparation of Zinc (II) 3-[[[Bis(carboxymethyl)amino]-acetyl]amino]propyl Magnetic Silica Particles.

Zinc (II) 3-[[[bis(carboxymethyl)amino]-acetyl]amino]-propyl magnetic silica particles were prepared by suspending 100 mg of a 3-[[[bis(carboxymethyl)amino]-acetyl]

amino]-propyl magnetic silica particles, prepared as described above, in a ZnCl$_2$ (250 mM) solution for two minutes at room temperature. The zinc solution was removed and the resulting magnetic silica particles were washed three times with water.

Example 2

Preparation of Metal-Modified 3-[[[Bis(carboxymethyl)amino] acetyl]-amino]propyl Silica Gel.

(a) Preparation Of 3-Aminopropyl-Modified Silica Gel.

3-Aminopropyltrimethoxysilane (125 mL) was added to a stirred solution of methanol (2000 mL) followed by addition of water (125 mL). This mixture was added to 250 g of silica gel (S10040T, 1000 angstom, Silicycle, Inc, Quebec, Canada) and the resulting mixture was kept in suspension for 4 hr at room temperature. After allowing the resin to settle the residual methanol/silane/water solution was decanted, the particles were washed with water (3×2.5 L) and resuspended in 2 L of methanol. The aminosilane-modified solid support was collected by filtration and dried under vacuum. Elemental analysis confirmed the composition of aminopropyl-modified solid support: C, 0.46; H, 0.30; N, 0.19.

(b) Preparation of 3-[[[Bis(carboxymethyl)amino]acetyl]amino]-propyl Silica Gel.

3-Aminopropyl-modified solid support (100 g) prepared as described above was suspended in N,N-dimethylacetamide (100 mL) and triethylamine (31 mL, 210 mmoles) was added to the mixture. This suspension was mixed thoroughly then 200 mmoles of 2,6-diketo-N-carboxymethylmorpholine (prepared according to U.S. Pat. No. 3,621,018, the contents of which are incorporated herein in its entirety) in 400 mL of N,N-dimethylacetamide was added and the resulting mixture was kept in suspension for 4 hr at room temperature. The unreacted N,N-dimethylacetamide/anhydride/triethylamine solution was removed and the solid support was washed with 4×1.2 L of water. Elemental analysis confirmed the composition of 3-[[[bis(carboxymethyl)amino] acetyl]amino]propyl solid support: C, 0.94; H, 0.32; N, 0.28.

(c) Preparation of Nickel (II) 3-[[[Bis(carboxymethyl)amino]acetyl]-amino]propyl Silica Gel.

A portion of 3-[[[bis(carboxymethyl)amino]acetyl]amino]propyl solid support prepared as described above was suspended in 250 mM nickel (II) chloride solution for 4 hr at room temperature. The excess nickel solution was removed and the resulting solid support was washed 5 times with water.

Example 3

Preparation of Propylethylenediamine-Modified Magnetic Silica Particles.

N-[3-(Trimethoxysilyl)propyl]ethylenediamine (2 mL) was added to a stirred solution of magnetic silica particles (2 g) in 95% methanol (8 mL). The resulting mixture was kept in suspension for 4 hr at room temperature. The residual methanol/silica solution was removed and the particles were washed with methanol (5×40 mL) and dried under vacuum. Elemental analysis confirmed the composition of aminopropylethylenediamine-modified silica magnetic solid support: C, 0.97; H, 0.70; N, 0.45.

Example 4

Preparation of Propylethylenediamine-Modified Silica Gel.

N-[3-(Trimethoxysilyl)propyl]ethylenediamine (2 mL) was added to a stirred solution of silica particles (1.0 g of Davisil, grade 644 silica gel, 100–200 mesh, 150 A pore size) in 95% methanol (8 mL). The resulting mixture was kept in suspension for 4 hr at room temperature. The residual methanol/silica solution was removed and the particles were washed with methanol, 5×40 mL, and dried under vacuum. Elemental analysis confirmed the composition of aminopropylethylenediamine-modified silica solid support: C, 5.82; H, 1.49; N, 2.44.

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

What is claimed is:

1. A composition comprising:

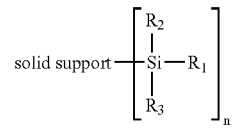

wherein R$_1$ is

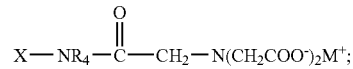

X is a substituted or unsubstituted alkylene moiety, a substituted or unsubstituted aralkylene moiety, or a substituted or unsubstituted arylene moiety;

R$_2$ and R$_3$ are independently selected from R$_1$, a hydrocarbon moiety, a substituted hydrocarbon moiety, a halogen atom, a hydrogen atom, a hydroxy, an alkoxy, a thiol, an amine, a silanol bond to the solid support, a bond to another silane ligand, or O—Si—Y$_1$Y$_2$Y$_3$, wherein Y$_1$, Y$_2$ and Y$_3$ are independently selected from a hydrocarbon moiety or a substituted hydrocarbon moiety;

R$_4$ is a hydrocarbon moiety, a substituted hydrocarbon moiety, or a hydrogen atom;

M is a metal ion; and n is an integer $\geq 1$.

2. The composition of claim 1, wherein the metal ion has an oxidation state of +1 to +6.

3. The composition of claim 2, wherein the metal ion is nickel, copper, cobalt, iron, zinc or gallium.

4. The composition of claim 1, wherein X is a saturated alkylene group or a substituted saturated alkylene group.

5. The composition of claim 1, wherein X is a saturated alkylene group of up to 10 carbon atoms or a substituted saturated alkylene group of up to 10 carbon atoms.

6. The composition of claim 5, wherein X is —(CH$_2$)$_3$—.

7. The composition of claim 1, wherein the solid support is selected from the group consisting of silica gels, siliceous oxides, solid silicas, magnetic silica particles, crystalline silicas, vitreous silicas, aluminum oxide, and combinations thereof.

8. A composition comprising

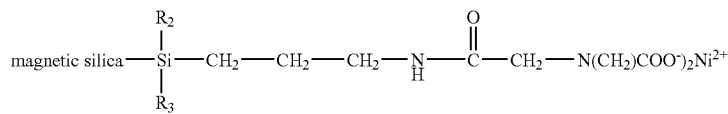

wherein $R_2$ and $R_3$ are independently selected from $R_1$, a hydrocarbon moiety, a substituted hydrocarbon moiety, a halogen atom, a hydrogen atom, a hydroxy, an alkoxy, a thiol, an amine, a silanol bond to the solid support, a bond to another silane ligand, or $O-Si-Y_1Y_2Y_3$, wherein $Y_1$, $Y_2$ and $Y_3$ are independently selected from a hydrocarbon moiety or a substituted hydrocarbon moiety.

9. A method of making a modified solid support comprising:

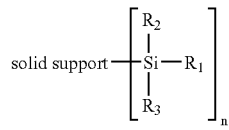

wherein $R_1$ is

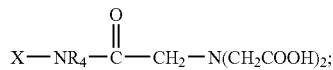

X is a substituted or unsubstituted alkylene moiety, a substituted or unsubstituted aralkylene moiety, or a substituted or unsubstituted arylene moiety;

$R_2$ and $R_3$ are independently selected from $R_1$, a hydrocarbon moiety, a substituted hydrocarbon moiety, a halogen atom, a hydrogen atom, a hydroxy, a thiol, an amine, a silanol bond to the solid support, a bond to another silane ligand, or $O-Si-Y_1Y_2Y_3$, wherein $Y_1$, $Y_2$ and $Y_3$ are independently selected from a hydrocarbon moiety or a substituted hydrocarbon moiety;

$R_4$ is a hydrocarbon moiety, a substituted hydrocarbon moiety, or a hydrogen atom; and n comprises an integer $\geq 1$, comprising:

(a) contacting a solid support with an aminosilane compound to form a first complex, having a silanol bond between the solid support and the aminosilane compound;

(b) contacting the first complex with nitrilotriacetic acid to form a modified solid support having an amide bond between the nitrilotriacetic acid and the first complex; and (c) contacting the modified solid support with a metal ion solution to form a metal-modified solid support.

10. The method of claim 9, wherein the aminosilane compound contains a saturated alkylene chain or a substituted saturated alkylene chain.

11. The method of claim 9, wherein the aminosilane compound is aminopropylsilane.

12. The method of claim 9, wherein the aminosilane compound is selected from the group consisting of aminopropylsilane, propylethylenediaminosilane, and aminopropyltrimethoxysilane compounds.

13. The method of claim 9, wherein the solid support is selected from the group consisting of silica gels, siliceous oxides, solid silicas, magnetic silica particles, crystalline silicas, vitreous silicas, aluminum oxide, and combinations thereof.

14. The method of claim 9, wherein the metal ion has an oxidation state of +1 to +6.

15. The method of claim 14, wherein the metal ion is nickel, copper, cobalt, iron, zinc or gallium.

16. A composition prepared by the process of claim 9.

* * * * *